US012765877B2

(12) United States Patent
Shi et al.

(10) Patent No.: US 12,765,877 B2
(45) Date of Patent: Oct. 20, 2026

(54) LIGATING CLIP FOR CONTINUOUS FIRING

(71) Applicant: HangZhou Sunstone Technology Co., Ltd., Zhejiang (CN)

(72) Inventors: Lei Shi, Hangzhou (CN); Hongjing Huang, Hangzhou (CN); Xiongquan Chen, Hangzhou (CN); Yanli Ma, Hangzhou (CN); Xiaorong Chen, Hangzhou (CN); Yuzhu Chen, Hangzhou (CN); Yaxue Weng, Hangzhou (CN); Dongfang Hu, Hangzhou (CN); Dongqiu Mei, Hangzhou (CN)

(73) Assignee: Hangzhou Sunstone Technology Co., LTD, Hangzhou (CN)

( * ) Notice: Subject to any disclaimer, the term of this patent is extended or adjusted under 35 U.S.C. 154(b) by 208 days.

(21) Appl. No.: 18/413,909

(22) Filed: Jan. 16, 2024

(65) Prior Publication Data

US 2024/0156465 A1 May 16, 2024

Related U.S. Application Data

(63) Continuation of application No. PCT/CN2022/105689, filed on Jul. 14, 2022.

(30) Foreign Application Priority Data

Mar. 24, 2022 (CN) ........................ 202210297955.2

(51) Int. Cl.
*A61B 17/122* (2006.01)

(52) U.S. Cl.
CPC ................................ *A61B 17/1222* (2013.01)

(58) Field of Classification Search
CPC .............. A61B 17/1222; A61B 17/105; A61B 17/1285; A61B 17/128; A61B 17/122;
(Continued)

(56) References Cited

U.S. PATENT DOCUMENTS 4,361,229 A * 11/1982 Mericle .............. A61B 17/1222 606/143
4,971,198 A * 11/1990 Mericle .............. A61B 17/1222 206/339
5,551,214 A * 9/1996 Vincze .................... B65B 5/105 53/471

FOREIGN PATENT DOCUMENTS

CN 104490445 A * 4/2015 ......... A61B 17/1222
CN 106037865 A * 10/2016 ......... A61B 17/1222

* cited by examiner

*Primary Examiner* — Katherine H Schwiker
(74) *Attorney, Agent, or Firm* — Honigman LLP; Matthew H. Szalach

(57) ABSTRACT

The invention provides a ligating clip for continuous firing and a process, which can arrange a plurality of ligating clips diastolically and orderly in the same direction and fix them in a continuous firing cartridge; Moreover, the ligating clip in the cartridge can be compressed to the allowable range of the puncture cannula by directionally moving the continuous firing cartridge in the cartridge sleeve, and the continuous firing cartridge can be separated from the cartridge sleeve; Alternatively, after the positioning guide post is arranged on the side cartridge, the positioning guide post is provided with a positioning groove, so the ligating clip is precisely positioned into the T-shaped upper slot between the first upper cartridge and the second upper cartridge, and the T-shaped lower slot between the first lower cartridge and the second lower cartridge, convenient to install the ligating clip while the ligating clip can be effectively positioned.

15 Claims, 8 Drawing Sheets

(58) Field of Classification Search
CPC .......... A61B 17/10; A61B 2017/07271; A61B 2017/0688
See application file for complete search history.

LIGATING CLIP FOR CONTINUOUS FIRING

CROSS-REFERENCE TO RELATED APPLICATIONS

This application is a continuation of PCT/CN2022/105689, filed Jul. 14, 2022 and claims priority of Chinese Patent Application No. 202210297955.2, filed on Mar. 24, 2022, the entire contents of which are incorporated herein by reference.

TECHNICAL FIELD

The invention belongs to the technical field of medical devices, in particular to a ligating clip for continuous firing.

BACKGROUND ART

In minimally invasive surgery, ligation clips are usually adopted to clip and close human tubular tissues, and special clamping instruments are required to be adopted together with the ligation clips. At present, the special clamping instruments for ligation clips are basically adopted by single installation. In an operation, it is usually necessary for a clip applier to repeatedly enter and exit the puncture hole of the human abdominal wall for the installation, closure and withdrawal of the ligating clip. The current installation method is manual single installation, with a low installation and application efficiency and a complicated installation and application process, which delays the operation time and increases the labor intensity. Alternatively, multiple and frequent entry and exit of the clip applier into the puncture hole of the human abdominal wall easily increase the risk of hospital infection of patients, and the tissue site to be clipped and closed needs to be repositioned after each entry into the body cavity, bringing inconvenience to the doctor's operation.

The cannula space of the abdominal wall puncture apparatus used in minimally invasive surgery is small, while the ligating clip has an irregular structure and a large size in the natural diastolic state, so that the ligating clip cannot pass through the puncture cannula. Only through the puncture cannula, the human tubular tissue can be ligated and closed in the compressed state after entering the body cavity.

Therefore, it is a difficult problem how a ligating clip can be pre-installed in a reusable continuous firing clip applier to achieve regular arrangement, and can be compressed when passing through the puncture cannula and then returned to a diastolic state when it is intended to be closed, and can be continuously transmitted and effectively closed in sequence.

CONTENT OF THE INVENTION

The first purpose of the invention is to provide a ligating clip for continuous firing in response to the above-mentioned technical problems.

Therefore, the above purpose of the invention is realized by the following technical scheme:

A ligating clip for continuous firing comprises a ligating clip and a continuous firing cartridge for holding the ligating clip, and the continuous firing cartridge comprises an upper cartridge assembly, a lower cartridge assembly matching with the upper cartridge assembly and a side cartridge;

The upper cartridge assembly comprises a first upper cartridge and a second upper cartridge, and the first upper cartridge and the second upper cartridge are spliced left and right to form an upper chamber of the ligating clip;

The lower cartridge assembly comprises a first lower cartridge and a second lower cartridge, and the first lower cartridge and the second lower cartridge are spliced left and right to form a lower holding chamber of the ligating clip;

The side cartridge is provided with a first moving part and a second moving part, the first upper cartridge can be disassembled and fixed to the first moving part of the side cartridge, the first lower cartridge can be disassembled and fixed to the second moving part of the side cartridge, and an upper and lower clamping mechanism is arranged between the upper cartridge assembly and the lower cartridge assembly;

The relative movement between the first moving part and the second moving part drives the upper cartridge assembly to compress the ligating clip between the upper cartridge assembly and the lower cartridge assembly relative to the lower cartridge assembly, and the upper cartridge assembly is fastened to the lower cartridge assembly at the same time; in the initial state, the first moving part and the second moving part are arranged so that the ligating clip is in a stretched state, and the opening of the ligating clip is at 60° to 120°. Within this opening range, the ligating clip can remain resilient for a long time after the upper and lower cartridge assemblies are closed and compressed;

The side cartridge is provided with a positioning guide post, a positioning groove is positioned in the positioning guide post, and the first upper cartridge and the first lower cartridge are provided with a positioning guide post hole matching with the positioning guide post, so that the first upper cartridge and the first lower cartridge can be dismounted and fixed to the side cartridge;

A T-shaped upper slot is formed between the first upper cartridge and the second upper cartridge, and a T-shaped lower slot is formed between the first lower cartridge and the second lower cartridge;

The positioning groove is adopted to limit the upper arm skirt pile gripper or lower arm skirt pile gripper for fixing the ligating clip and locate the ligating clip to the T-shaped upper groove formed between the first upper cartridge and the second upper cartridge and the T-shaped lower groove formed between the first lower cartridge and the second lower cartridge.

While adopting the technical scheme, the invention can also adopt or combine the following technical schemes:

As the preferred technical scheme of the invention, a guide mechanism is arranged between the first moving part and the second moving part of the side cartridge. The guide mechanism comprises a guide bin and a guide column, and the guide bin and the guide column are coordinated to realize positioning compression between the upper cartridge assembly and the lower cartridge assembly;

The guide bin is semi-enclosed or fully enclosed.

As the preferred technical scheme of the invention:

The two ends of the first upper cartridge and the second upper cartridge are provided with a top side clamping mechanism to enable the first upper cartridge and the second upper cartridge to splice left and right;

The two ends of the first lower cartridge and the second lower cartridge are provided with a bottom side clamping mechanism to enable the first lower cartridge and the second lower cartridge to splice left and right.

As the preferred technical scheme of the invention:

The top of the first upper cartridge and the second upper cartridge are provided with a middle upper clamping mechanism to firmly splice the central part of the first upper cartridge and the second upper cartridge;

The bottom of the first lower cartridge and the second lower cartridge are provided with a middle lower clamping mechanism to firmly splice the central part of the first lower cartridge and the second lower cartridge.

As the preferred technical scheme of the invention:

The top of the first upper cartridge or the second upper cartridge is provided with a plurality of positioning columns, and the top of the second upper cartridge or the first upper cartridge is provided with positioning holes matching with the positioning columns;

The top of the first lower cartridge or the second lower cartridge is provided with a plurality of positioning columns, and the top of the second lower cartridge or the first lower cartridge is provided with positioning holes matching with the positioning columns.

As the preferred technical scheme of the invention, the ligating clip for continuous firing also comprises a cartridge sleeve;

The cartridge sleeve comprises a holding part and a cover plate, the holding part is adopted to accommodate the continuous firing cartridge, and the cover plate is adopted to close the holding part to form a wrap around the continuous firing cartridge with the holding part;

The cartridge sleeve is provided with at least one hollowout, which is adopted to assist in relatively pressing the continuous firing cartridge to compress the ligating clip in the continuous firing cartridge.

As the preferred technical solution of the invention, one side of the cover plate is hinged between the holding part of the cartridge sleeve.

As the preferred technical solution of the invention, a direct snap is formed between the cover plate and the holding part of the cartridge sleeve.

As the preferred technical scheme of the invention, positioning guide edges are arranged along the pressing direction of the continuous firing cartridge inside the cartridge sleeve, and the sides of the upper cartridge assembly and the lower cartridge assembly are provided with positioning guide grooves corresponding to the positioning guide edges.

The second purpose of the invention is to provide an assembly process of a ligating clip for continuous firing in view of the above-mentioned technical problems.

Therefore, the above purpose of the invention is realized by the following technical scheme:

The assembly process of a ligating clip for continuous firing is adopted to assemble a ligating clip for continuous firing as described above, including the following steps:

(1) The first upper cartridge in the upper cartridge assembly and the first lower cartridge in the lower cartridge assembly are disassembled and fixed to the side cartridge;

(2) Place ligating clips into the first upper cartridge of the upper cartridge assembly and the first lower cartridge of the lower cartridge assembly so that the upper arm skirt pile gripper and the lower arm skirt pile gripper of the ligating clip are limited and fixed to the positioning grooves of the positioning guide post on the side cartridge respectively. The positioning grooves are arranged to position the upper end and lower end of the ligating clip to the T-shaped upper groove formed between the first upper cartridge and the second upper cartridge, and the T-shaped lower groove formed between the first lower cartridge and the second lower cartridge respectively, so that the ligating clip is in a stretched state, and the opening of the ligating clip is at 60° to 120°;

(3) Splice the second upper cartridge of the upper cartridge assembly and the second lower cartridge of the lower cartridge assembly into the first upper cartridge of the upper cartridge assembly and the first lower cartridge of the lower cartridge assembly respectively;

(4) Compress the first moving part or the second moving part of the side cartridge so that the upper cartridge assembly or lower cartridge assembly moves relative to the lower cartridge assembly or upper cartridge assembly to close the ligating clips in the upper cartridge assembly and lower cartridge assembly, and close them until the upper and lower clamping mechanisms between the upper cartridge assembly and the lower cartridge assembly are stuck to the upper cartridge assembly and the lower cartridge assembly before they are completely closed;

(5) Remove the side cartridge from the side of the upper cartridge assembly and the lower cartridge assembly to obtain a fully closed cartridge that can be placed into the continuous firing clip applier.

The invention provides a ligating clip for continuous firing and a process, which can arrange a plurality of ligating clips in a diastolic state and an orderly sequence in the same direction and fix them in a continuous firing cartridge; Moreover, the ligating clip in the cartridge can be compressed to the allowable range of the puncture cannula by directional movement of the continuous firing cartridge in the cartridge sleeve, and the continuous firing cartridge can be separated from the cartridge sleeve; Alternatively, after the positioning guide post is arranged on the side cartridge, the positioning guide post is provided with a positioning groove, so that the ligating clip is precisely positioned into a T-shaped upper slot between the first upper cartridge and the second upper cartridge, and a T-shaped lower slot between the first lower cartridge and the second lower cartridge, which is convenient to install the ligating clip and at the same time the ligating clip can be effectively positioned.

DRAWING LEGENDS

CONCRETE IMPLEMENTATION MODE

The invention is further described in detail with reference to the attached drawings and specific embodiments.

Figure 1:
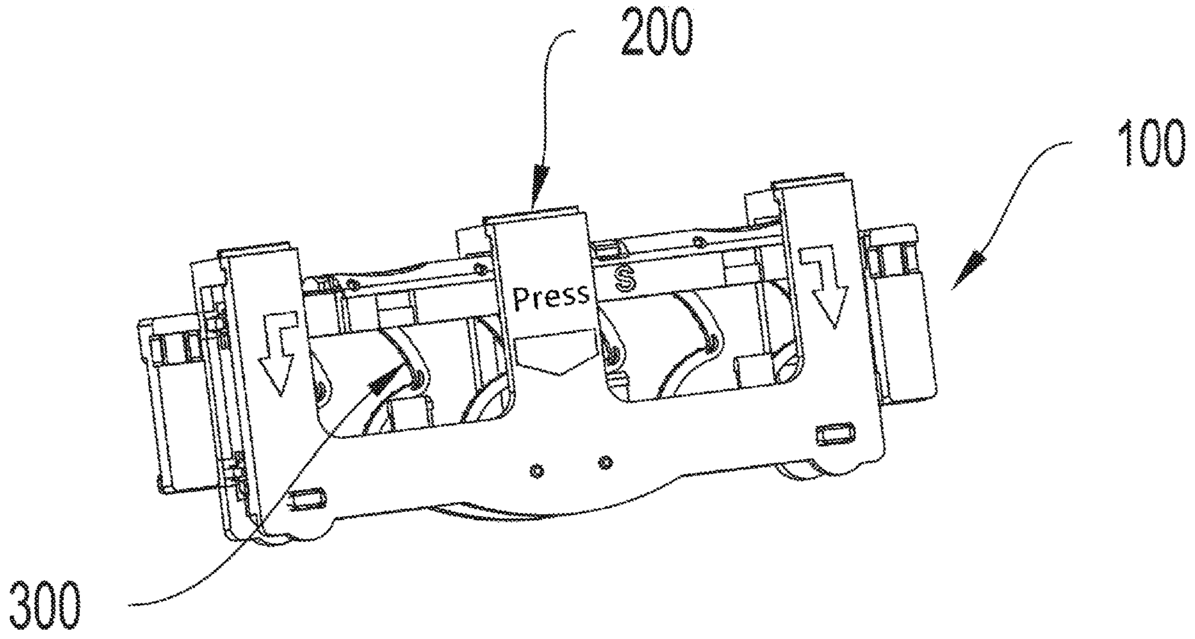
FIG. 1 is an overall illustration of the ligating clip for continuous firing including a cartridge sleeve provided by the invention.
Figure 2:
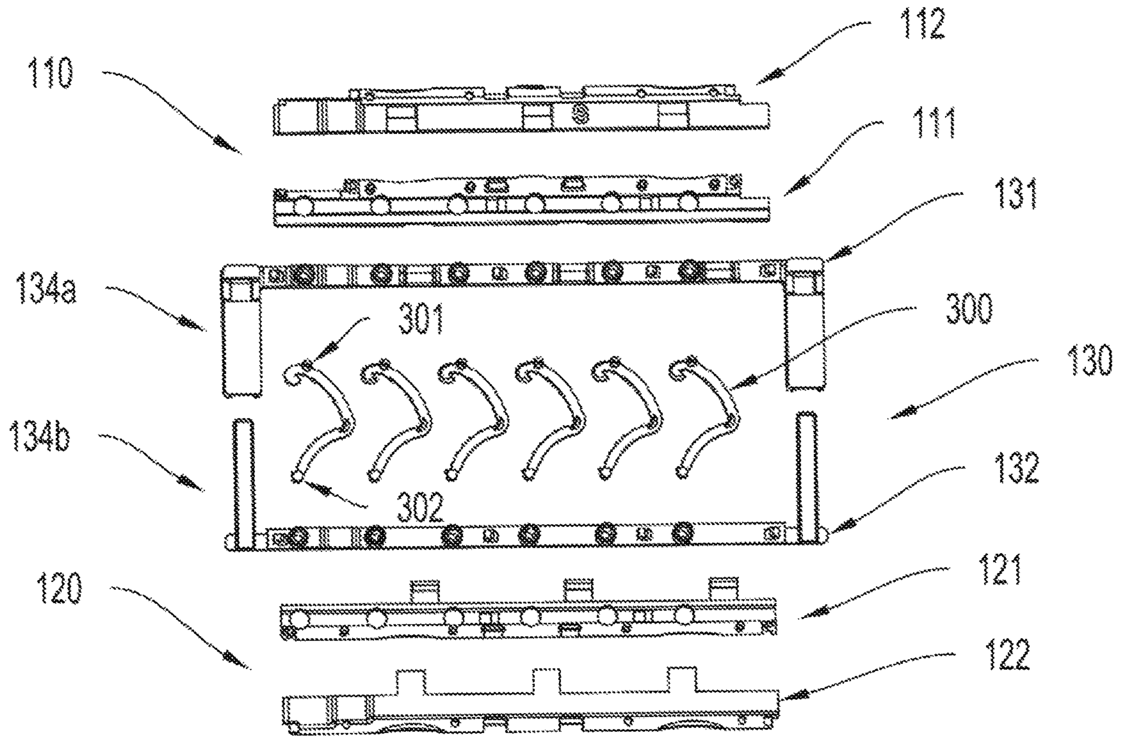
FIG. 2 shows the overall representation of the continuous firing cartridge.
Figure 3:
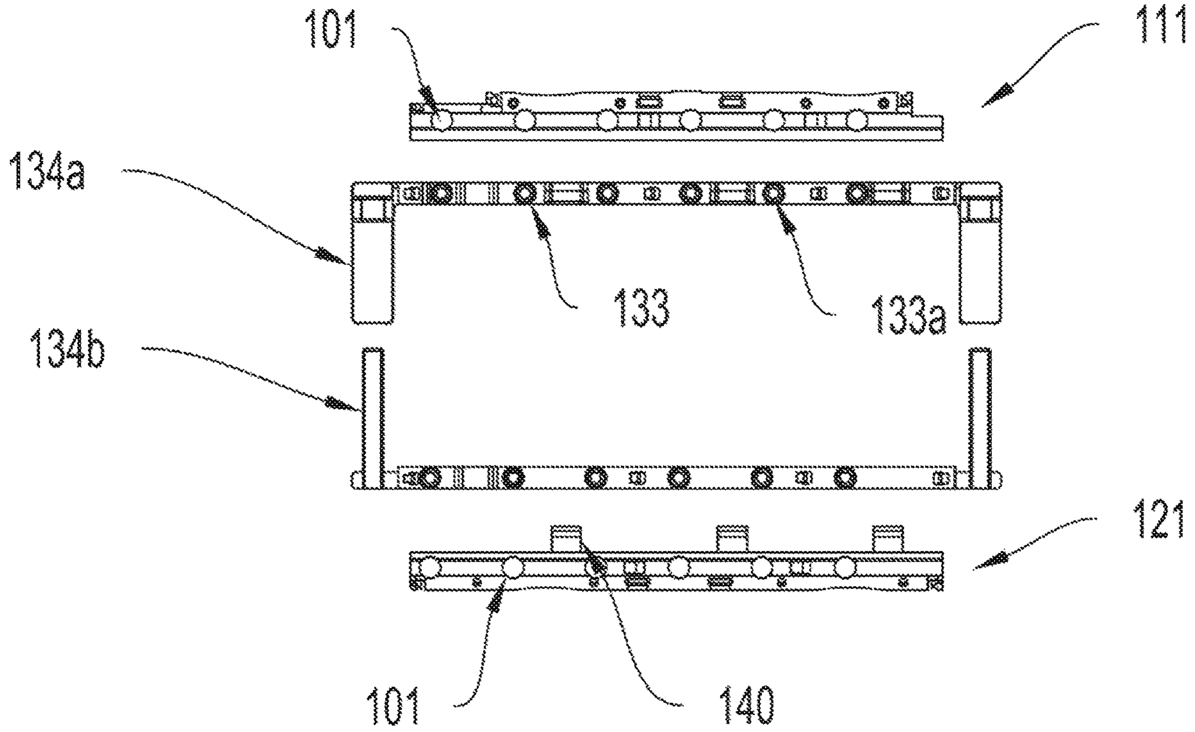
FIG. 3 shows the connection diagram of the first upper cartridge, the first lower cartridge and the side cartridge.
Figure 4:
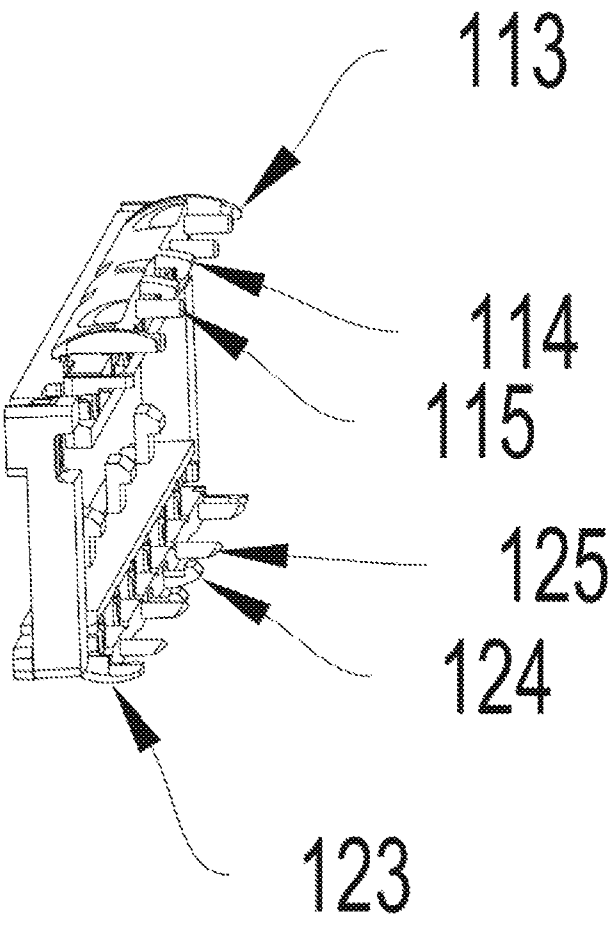
FIG. 4 shows the side view of the connection of the first upper cartridge, first lower cartridge and side cartridge.
Figure 5:
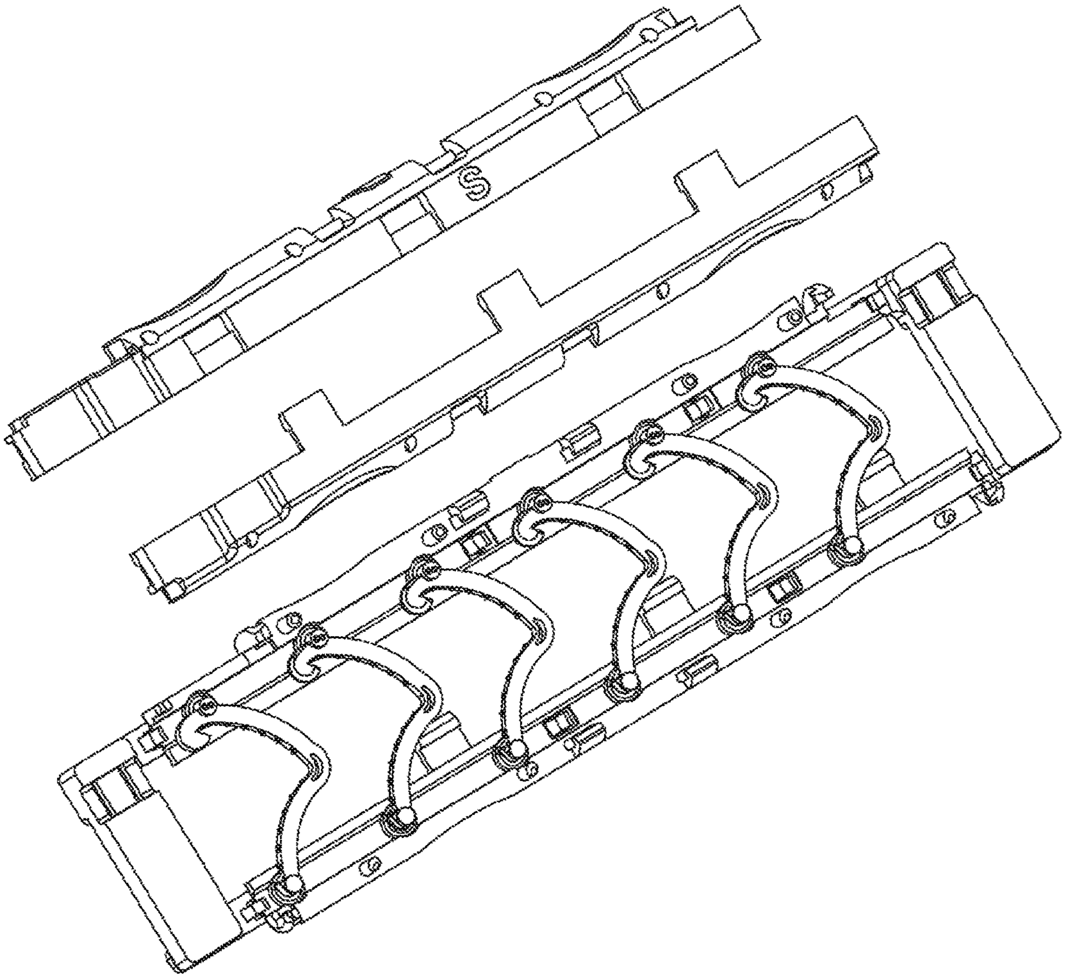
FIG. 5 shows the assembly process of the upper cartridge assembly, lower cartridge assembly and side cartridge.
Figure 6:
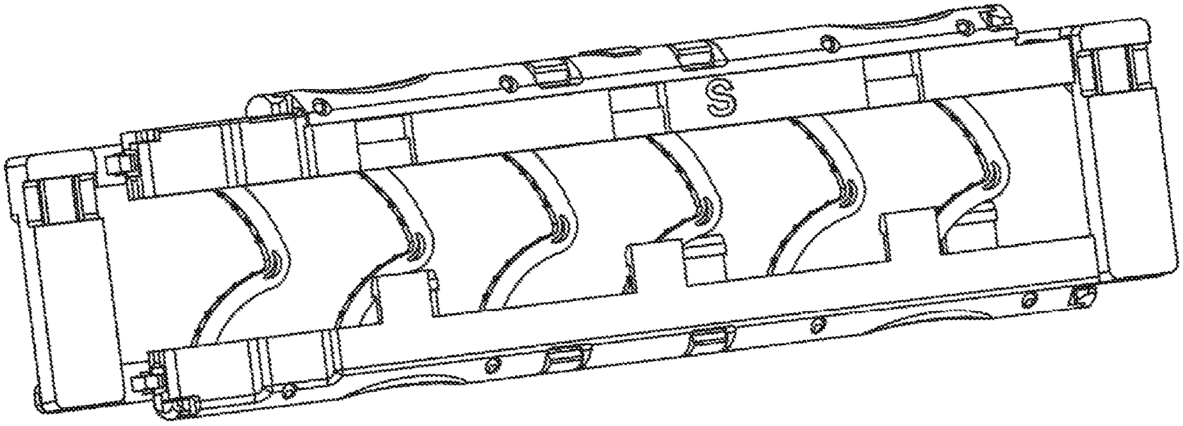
FIG. 6 shows the assembled upper cartridge assembly, lower cartridge assembly, and side cartridge.
Figure 7:
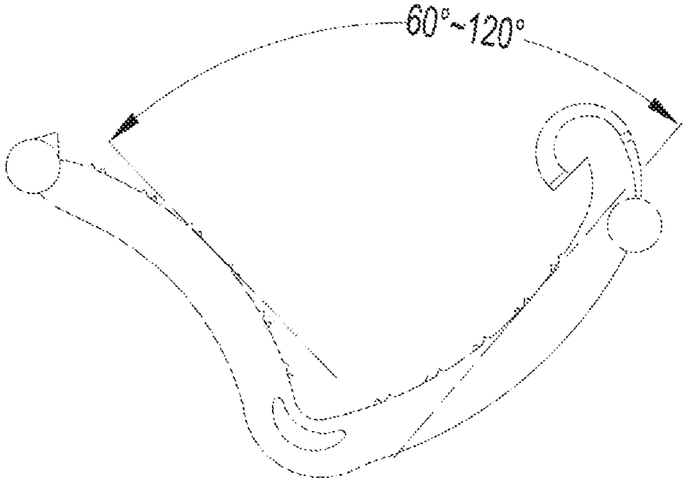
FIG. 7 shows the ligating clip in the stretched state.
Figure 8:
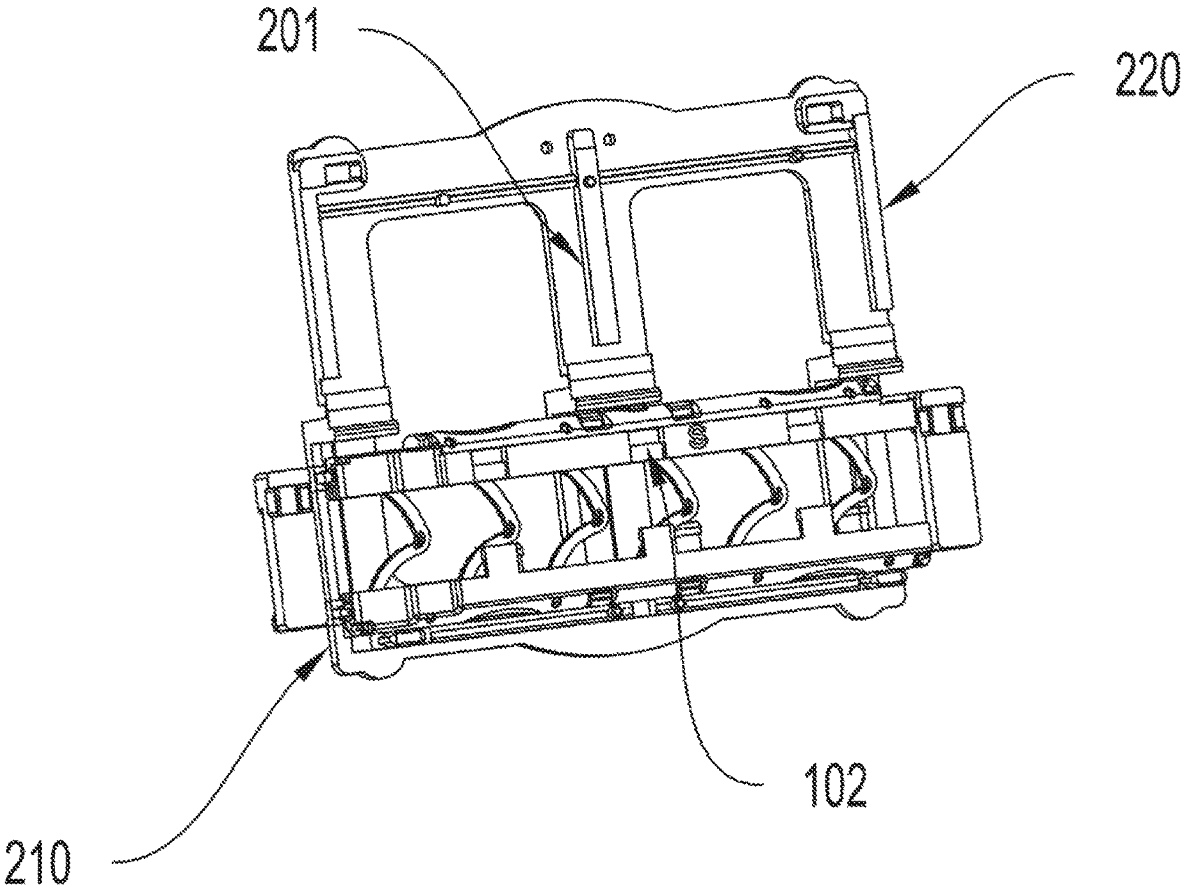
FIG. 8 shows the assembly diagram of the continuous firing cartridge and cartridge sleeve.
Figure 9:
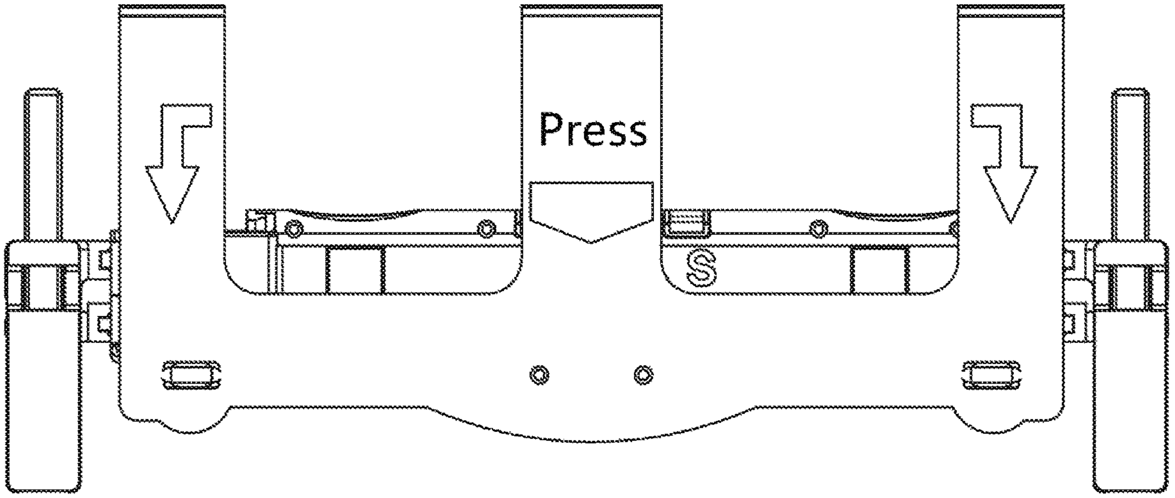
FIG. 9 shows the process of pressing with ligating clips.
Figure 10:
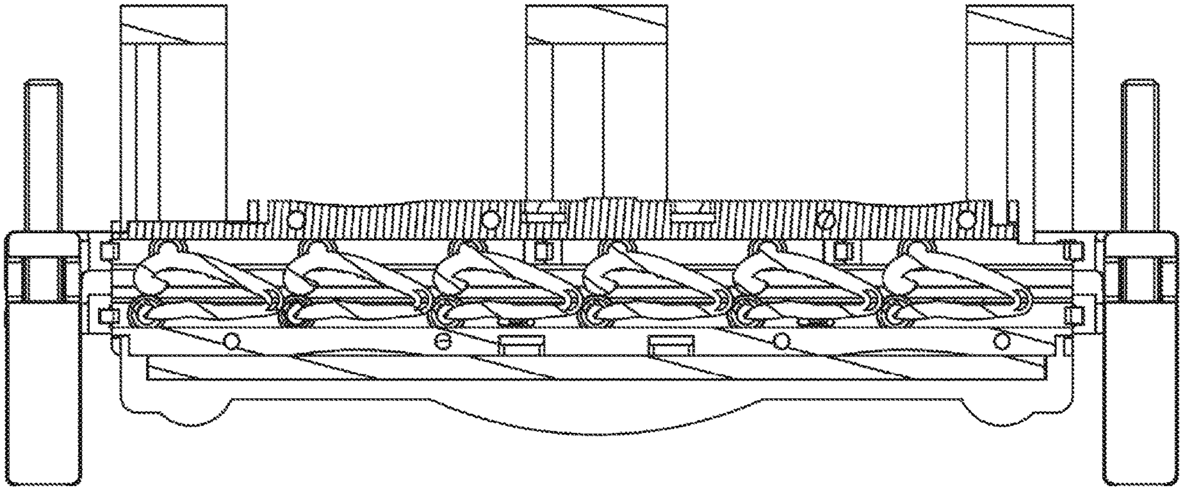
FIG. 10 is a half profile of FIG. 9.
Figure 11:
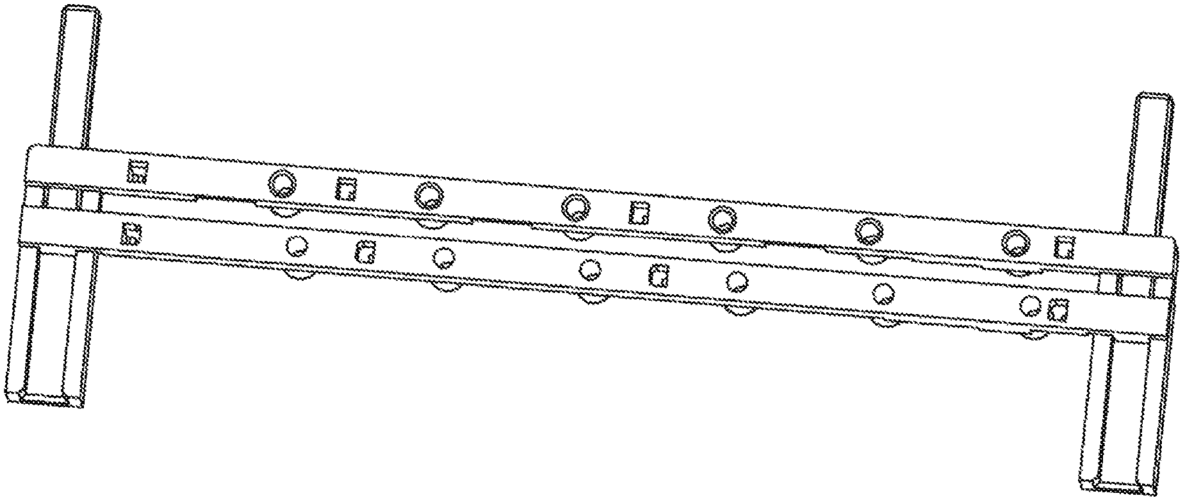
FIG. 11 shows the side cartridge after removal.
Figure 12:
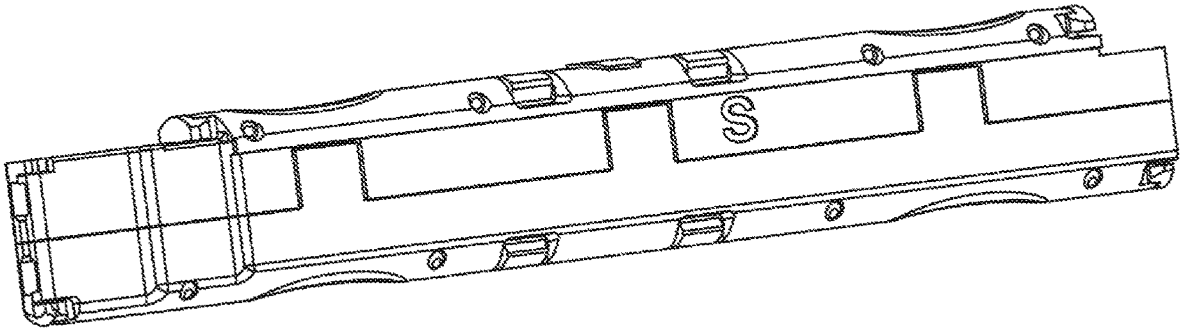
FIG. 12 shows the continuous firing cartridge after removing the side cartridge.

Referring to FIGS. 1 to 12, a ligating clip for continuous firing for loading a ligating clip 300 comprises a ligating clip 300 and a continuous firing cartridge 100 for holding the ligating clip 300, and the continuous firing cartridge 100 comprises an upper cartridge assembly 110, a lower cartridge assembly 120 matching with an upper cartridge assembly 110, and a side cartridge 130;

The front and back ends of the continuous firing cartridge are provided with a clip table fixed with the continuous firing clip applier;

The upper cartridge assembly 110 comprises a first upper cartridge 111, a second upper cartridge 112, and the first upper cartridge 111 and the second upper cartridge 112 are spliced left and right to form an upper holding chamber of the ligating clip 300;

The lower cartridge assembly 120 comprises a first lower cartridge 121 and a second lower cartridge 122, and the first lower cartridge 121 and the second lower cartridge 122 are spliced left and right to form a lower holding chamber of the ligating clip 300;

The side cartridge is provided with a first moving part 131 and a second moving part 132, the first upper cartridge 111 can be disassembled and fixed to the first moving part 131 of the side cartridge 130, the first lower cartridge 121 can be disassembled and fixed to the second moving part 132 of the side cartridge 130, and an upper and lower clamping mechanism 140 is provided between the upper cartridge assembly 110 and the lower cartridge assembly 120, such as a clip fastener;

The relative movement between the first moving part 131 and the second moving part 132 drives the upper cartridge assembly 110 to compress the ligating clip 300 between the upper cartridge assembly 110 and the lower cartridge assembly 120 relative to the lower cartridge assembly 120, and the upper cartridge assembly 110 is fastened to the lower cartridge assembly 120 at the same time. In the initial state, the first moving part 131 and the second moving part 132 are arranged so that the ligating clip 3 is in a stretched state, and the opening of the ligating clip is at 60° to 120°. Within this opening range, the ligating clip can remain resilient for a long time after the upper cartridge assembly and lower cartridge assembly are closed and compressed.

The side cartridge 130 is provided with a positioning guide post 133, a positioning groove 133*a* is positioned in the positioning guide post 133, and the first upper cartridge 111 and the first lower cartridge 121 are provided with a positioning guide post hole 101 matching with the positioning guide post 133, so that the first upper cartridge 111 and the first lower cartridge 121 can be dismounted and fixed to the side cartridge 130. The side cartridge can be connected to the first upper cartridge and the first lower cartridge by means of a full fit or a hole-column fit or a clip fastener (such as, the form of a plurality of clip fasteners arranged on the side cartridge), and of course, in other embodiments.

A T-shaped upper slot is formed between the first upper cartridge 111 and the second upper cartridge 112, and a T-shaped lower slot is formed between the first lower cartridge 121 and the second lower cartridge 122;

The positioning groove 133*a* is adopted to limit the upper arm skirt pile gripper 301 or lower arm skirt pile gripper 302 for fixing the ligating clip 300 and locate the ligating clip 300 to the T-shaped upper slot formed between the first upper cartridge 111 and the second upper cartridge 112 and the T-shaped lower slot formed between the first lower cartridge 121 and the second lower cartridge 122.

A guide mechanism is arranged between the first moving part 131 and the second moving part 132 of the side cartridge 130. The guide mechanism comprises a guide bin 134*a* and a guide column 134*b*. The guide bin 134*a* is coordinated with the guide column 134*b* to realize positioning compression between the upper cartridge assembly 110 and the lower cartridge assembly 120;

The guide bin 134*a* is semi-enclosed or fully enclosed.

The two ends of the first upper cartridge 111 and the second upper cartridge 112 are provided with a top side clamping mechanism 113 which is a snap-fit structure with protrusions/claws acting as elastic parts coupled with slots/recesses acting as mating parts which when combined with positioning elements, such as locating pins and locating holes achieve the functionality of a secure fixation after assembly and reversible separation during disassembly to enable the first upper cartridge 111 and the second upper cartridge 112 to splice left and right; the two ends of the first lower cartridge 121 and the second lower cartridge 122 are provided with a bottom side clamping mechanism 123 which is a snap-fit structure with protrusions/claws acting as elastic parts coupled with slots/recesses acting as mating parts which when combined with positioning elements, such as locating pins and locating holes achieve the functionality of a secure fixation after assembly and reversible separation during disassembly to enable the first lower cartridge 121 and the second lower cartridge 122 to splice left and right.

The top of the first upper cartridge 111 and the second upper cartridge 112 are provided with a middle upper clamping mechanism 114 which is a snap-fit structure with protrusions/claws acting as elastic parts coupled with slots/recesses acting as mating parts which when combined with positioning elements, such as locating pins and locating holes achieve the functionality of a secure fixation after assembly and reversible separation during disassembly to firmly splice the central part of the first upper cartridge 111 and the second upper cartridge 112; the bottom of the first lower cartridge 121 and the second lower cartridge 122 are provided with a middle lower clamping mechanism 124 which is a snap-fit structure with protrusions/claws acting as elastic parts coupled with slots/recesses acting as mating parts which when combined with positioning elements, such as locating pins and locating holes achieve the functionality of a secure fixation after assembly and reversible separation during disassembly to firmly splice the central part of the first lower cartridge 121 and the second lower cartridge 122.

The top of the first upper cartridge 111 or the second upper cartridge 112 is provided with a plurality of positioning columns 115, and the top of the second upper cartridge 112 or the first upper cartridge 111 is provided with positioning holes 116 matching with the positioning columns;

The top of the first lower cartridge 121 or the second lower cartridge 122 is provided with a plurality of positioning columns 125, and the top of the second lower cartridge 122 or the first lower cartridge 121 is provided with positioning holes 126 matching with the positioning columns.

The ligating clip for continuous firing also includes a cartridge sleeve 200,

The cartridge sleeve 200 comprises a holding part 210 which is a snap-fit structure with protrusions/claws acting as elastic parts coupled with slots/recesses acting as mating parts which when combined with positioning elements, such as locating pins and locating holes achieve the functionality of a secure fixation after assembly and reversible separation during disassembly and a cover plate 220, the holding part 210 is adopted to accommodate the continuous firing cartridge 100, and the cover plate 220 is adopted to close the holding part 210 to form a wrap around the continuous firing cartridge 100 with the holding part 210;

The cartridge sleeve 200 is provided with at least one hollowout 201, which is adopted to assist in relatively pressing the continuous firing cartridge 100 to compress the ligating clip 300 in the continuous firing cartridge 100.

One side of the cover plate 220 is hinged with the holding part 210 of the cartridge sleeve 200 or a direct snap is formed between the cover plate 220 and the holding part 210 of the cartridge sleeve 200.

Positioning guide edges 201 are arranged along the pressing direction of the continuous firing cartridge 100 inside the cartridge sleeve 200, and the sides of the upper cartridge assembly 110 and the lower cartridge assembly 120 of the continuous firing cartridge 100 are provided with positioning guide grooves 102 corresponding to the positioning guide edges 201.

In the embodiment, the cartridge sleeve 200 is box-frame, and the box frame is flipped open or closed. Definitely, in other embodiments, it can also be closed by direct fastening. Open the box frame, that is, open the cover body 220, and place the continuous firing cartridge containing the ligating clip into the holding part 210 of the cartridge sleeve 200 along the positioning guide edge 201. At this time, the upper cartridge assembly and the lower cartridge assembly are in a separate state (or unfolded state); Close the box frame, and compress the upper cartridge assembly or the lower cartridge assembly from the hollowout, so that the upper cartridge assembly and the lower cartridge assembly are relatively compressed and merged, and are fastened with the upper clamping mechanism between the upper cartridge assembly and the lower cartridge assembly; the continuous firing cartridge is taken out from the cartridge sleeve and the side cartridge is removed from the side, and the closed continuous firing cartridge is formed to arrange the ligating clips in the continuous firing cartridge a diastolic state and an orderly sequence in the same direction. Then the continuous firing cartridge is placed into the continuous firing clip applier through the clip table on the continuous firing cartridge. The T-shaped slot inside the continuous firing cartridge is connected with the conveying channel of the continuous firing clip applier, so that the semi-closed ligating clips arranged in the slot can be transported to the continuous firing clip applier in an orderly manner in turn.

In the embodiment, the ligating clip for continuous firing with a cartridge sleeve is shown. Alternatively, no cartridge sleeve may be used. In the absence of a cartridge sleeve, the upper and lower cartridge assemblies may be closed by compressing the multiple ligating clips between the upper cartridge assembly and lower cartridge assembly directly through the guide mechanism of the side cartridge, such as by the following assembly process:

(1) The first upper cartridge in the upper cartridge assembly and the first lower cartridge in the lower cartridge assembly are disassembled and fixed to the side cartridge;

(2) Place ligating clips into the first upper cartridge of the upper cartridge assembly and the first lower cartridge of the lower cartridge assembly so that the upper arm skirt pile gripper and the lower arm skirt pile gripper of the ligating clip are limited and fixed to the positioning grooves of the positioning guide post on the side cartridge respectively. The positioning grooves are arranged to position the upper end and lower end of the ligating clip to the T-shaped upper groove formed between the first upper cartridge and the second upper cartridge, and the T-shaped lower groove formed between the first lower cartridge and the second lower cartridge respectively, so that the ligating clip is in a stretched state, and the opening of the ligating clip is at 60° to 120°;

(3) Splice the second upper cartridge of the upper cartridge assembly and the second lower cartridge of the lower cartridge assembly into the first upper cartridge of the upper cartridge assembly and the first lower cartridge of the lower cartridge assembly respectively;

(4) Compress the first moving part or the second moving part of the side cartridge so that the upper cartridge assembly or lower cartridge assembly moves relative to the lower cartridge assembly or upper cartridge assembly to close the ligating clips in the upper cartridge assembly and lower cartridge assembly, and close them until the upper and lower clamping mechanisms between the upper cartridge assembly and the lower cartridge assembly are stuck to the upper cartridge assembly and the lower cartridge assembly before they are completely closed;

(5) Remove the side cartridge from the side of the upper cartridge assembly and the lower cartridge assembly to obtain a fully closed cartridge that can be placed into the continuous firing clip applier.

The above specific embodiments are adopted to explain the invention and are only preferred embodiments of the invention, rather than restrictions on the invention. Any modification, equivalent replacement, improvement, etc. made to the invention within the scope of protection of the invention and the claims of the invention shall fall within the scope of protection of the invention.

The invention claimed is:

1. A system for continuous firing comprises a ligating clip and a continuous firing cartridge for holding the ligating clip, and is characterized in that the continuous firing cartridge comprises an upper cartridge assembly, a lower cartridge assembly matched with the upper cartridge assembly and a side cartridge;

The upper cartridge assembly comprises a first upper cartridge and a second upper cartridge, and the first upper cartridge and the second upper cartridge are spliced left and right to form an upper chamber for the ligating clip;

The lower cartridge assembly comprises a first lower cartridge and a second lower cartridge, and the first lower cartridge and the second lower cartridge are spliced left and right to form a lower holding chamber for the ligating clip;

The side cartridge is provided with a first moving part and a second moving part, the first upper cartridge can be disassembled and fixed to the first moving part of the side cartridge, the first lower cartridge can be disassembled and fixed to the second moving part of the side cartridge, and a snap-fit structure comprising protrusions configured to connect with recess slots is arranged between the upper cartridge assembly and the lower cartridge assembly;

relative movement between the first moving part and the second moving part drives the upper cartridge assembly to compress the ligating clip between the upper cartridge assembly and the lower cartridge assembly relative to the lower cartridge assembly, and the upper cartridge assembly is fastened to the lower cartridge assembly at the same time; In an initial state, the first moving part and the second moving part are arranged so that the ligating clip is in a stretched state, and an opening of the ligating clip is at 60° to 120°;

The side cartridge is provided with a positioning guide post, a positioning groove is positioned in the positioning guide post, and the first upper cartridge and the first lower cartridge are provided with a positioning guide post hole matching with the positioning guide post, so that the first upper cartridge and the first lower cartridge can be dismounted and fixed to the side cartridge;

A T-shaped upper slot is formed between the first upper cartridge and the second upper cartridge, and a T-shaped lower slot is formed between the first lower cartridge and the second lower cartridge;

The positioning groove is adopted to limit and fix an upper arm skirt pile gripper or a lower arm skirt pile gripper for fixing the ligating clip and locate the ligating clip to the T-shaped upper slot formed between the first upper cartridge and the second upper cartridge and the T-shaped lower slot formed between the first lower cartridge and the second lower cartridge.

2. The system according to claim 1 wherein a guide mechanism is arranged between the first moving part and the second moving part of the side cartridge wherein the guide mechanism comprises a guide bin and a guide column, and the guide bin and the guide column are coordinated to realize positioning compression between the upper cartridge assembly and the lower cartridge assembly;

The guide bin is semi-enclosed or fully enclosed.

3. System according to claim 2 further comprising wherein the ligating clip for continuous firing also includes a cartridge sleeve, wherein The cartridge sleeve comprises a housingsnap-fit structure comprising protrusions configured to connect with recess slots and a cover plate, the housingsnap-fit structure comprising protrusions configured to connect with recess slots is adopted to accommodate the continuous firing cartridge, and the cover plate is adopted to close the housingsnap-fit structure comprising protrusions configured to connect with recess slots to form a wrap around the continuous firing cartridge with the housingsnap-fit structure comprising protrusions configured to connect with recess slots;

The cartridge sleeve is provided with at least one hollowout, which is adopted to assist in relatively pressing the continuous firing cartridge to compress the ligating clip in the continuous firing cartridge.

4. The system according to claim 1 wherein:

two ends of the first upper cartridge and the second upper cartridge are provided with a top side snap-fit structure comprising protrusions configured to connect with recess slots configured to enable the first upper cartridge and the second upper cartridge to splice left and right; and wherein two ends of the first lower cartridge and the second lower cartridge are provided with a bottom side snap-fit structure comprising protrusions configured to connect with recess slots configured to enable the first lower cartridge and the second lower cartridge to splice left and right.

5. The system according to claim 4 wherein:

a top of the first upper cartridge and the second upper cartridge are provided with a middle upper snap-fit structure comprising protrusions configured to connect with recess slots configured to firmly splice a central part of the first upper cartridge and the second upper cartridge;

a bottom of the first lower cartridge and the second lower cartridge are provided with a middle lower snap-fit structure comprising protrusions configured to connect with recess slots configured to firmly splice the central part of the first lower cartridge and the second lower cartridge.

6. The system according to claim 5 wherein:

a top of the first upper cartridge or the second upper cartridge is provided with a plurality of positioning columns, and the top of the other side of the second upper cartridge or the first upper cartridge is provided with positioning holes matching with the positioning columns;

The top of the first lower cartridge or the second lower cartridge is provided with a plurality of positioning columns, and the top of the second lower cartridge or the first lower cartridge is provided with positioning holes matching with the positioning columns.

7. The system according to claim 6 wherein positioning guide edges are arranged along a pressing direction of the continuous firing cartridge inside a cartridge sleeve, and sides of the upper cartridge assembly and the lower cartridge assembly of the continuous firing cartridge are provided with positioning guide grooves corresponding to the positioning guide edges.

8. The system according to claim 5 further comprising wherein the ligating clip for continuous firing also includes a cartridge sleeve, wherein The cartridge sleeve comprises a housingsnap-fit structure comprising protrusions configured to connect with recess slots and a cover plate, the housingsnap-fit structure comprising protrusions configured to connect with recess slots is adopted to accommodate the continuous firing cartridge, and the cover plate is adopted to close the housingsnap-fit structure comprising protrusions configured to connect with recess slots to form a wrap around the continuous firing cartridge with the housingsnap-fit structure comprising protrusions configured to connect with recess slots;

The cartridge sleeve is provided with at least one hollowout, which is adopted to assist in relatively pressing the continuous firing cartridge to compress the ligating clip in the continuous firing cartridge.

9. The system according to claim 4 wherein:

The top of the first upper cartridge or the second upper cartridge is provided with a plurality of positioning columns, and the top of the other side of the second upper cartridge or the first upper cartridge is provided with positioning holes matching with the positioning columns;

a top of the first lower cartridge or the second lower cartridge is provided with a plurality of positioning columns, and the top of the other side of the second lower cartridge or the first lower cartridge is provided with positioning holes matching with the positioning columns.

10. The system according to claim 9 further comprising wherein the ligating clip for continuous firing also includes a cartridge sleeve, wherein The cartridge sleeve comprises a housingsnap-fit structure comprising protrusions configured to connect with recess slots and a cover plate, the housingsnap-fit structure comprising protrusions configured to connect with recess slots is adopted to accommodate the continuous firing cartridge, and the cover plate is adopted to close the housingsnap-fit structure comprising protrusions configured to connect with recess slots to form a wrap around the continuous firing cartridge with the housingsnap-fit structure comprising protrusions configured to connect with recess slots;

The cartridge sleeve is provided with at least one hollowout, which is adopted to assist in relatively pressing the continuous firing cartridge to compress the ligating clip in the continuous firing cartridge.

11. The system according to claim 4 further comprising wherein the ligating clip for continuous firing also includes a cartridge sleeve, wherein The cartridge sleeve comprises a housingsnap-fit structure comprising protrusions configured to connect with recess slots and a cover plate, the housingsnap-fit structure comprising protrusions configured to connect with recess slots is adopted to accommodate the continuous firing cartridge, and the cover plate is adopted to close the housingsnap-fit structure comprising protrusions configured to connect with recess slots to form a wrap around the continuous firing cartridge with the housingsnap-fit structure comprising protrusions configured to connect with recess slots;

The cartridge sleeve is provided with at least one hollowout, which is adopted to assist in relatively pressing the continuous firing cartridge to compress the ligating clip in the continuous firing cartridge.

12. The system according to claim 1 further comprising wherein the ligating clip for continuous firing also includes a cartridge sleeve, wherein The cartridge sleeve comprises a housingsnap-fit structure comprising protrusions configured to connect with recess slots and a cover plate, the housingsnap-fit structure comprising protrusions configured to connect with recess slots is adopted to accommodate the continuous firing cartridge, and the cover plate is adopted to close the housingsnap-fit structure comprising protrusions configured to connect with recess slots to form a wrap around the continuous firing cartridge with the housingsnap-fit structure comprising protrusions configured to connect with recess slots;

The cartridge sleeve is provided with at least one hollowout, which is adopted to assist in relatively pressing the continuous firing cartridge to compress the ligating clip in the continuous firing cartridge.

13. The system according to claim 12 wherein one side of the cover plate is hinged with the housingsnap-fit structure comprising protrusions configured to connect with recess slots of a cartridge sleeve.

14. The system according to claim 12 wherein a direct snap is formed between the cover plate and the housingsnap-fit structure comprising protrusions configured to connect with recess slots of the cartridge sleeve.

15. An assembly process for a system for continuous firing of a ligating clip as defined in claim 1 comprising the steps of:

(1) The first upper cartridge in the upper cartridge assembly and the first lower cartridge in the lower cartridge assembly are disassembled and fixed to the side cartridge;

(2) Place a ligating clip into the first upper cartridge of the upper cartridge assembly and the first lower cartridge of the lower cartridge assembly so that the upper arm skirt pile gripper and the lower arm skirt pile gripper of the ligating clip are limited and fixed to the positioning groove of the positioning guide post on the side cartridge respectively wherein the positioning groove arranged to position an upper end and a lower end of the ligating clip to the T-shaped upper slot formed between the first upper cartridge and the second upper cartridge, and the T-shaped lower slot formed between the first lower cartridge and the second lower cartridge respectively, so that the ligating clip is in the stretched state, and the opening of the ligating clip is at 60° to 120°;

(3) Splice the second upper cartridge of the upper cartridge assembly and the second lower cartridge of the lower cartridge assembly into the first upper cartridge of the upper cartridge assembly and the first lower cartridge of the lower cartridge assembly respectively;

(4) Compress the first moving part or the second moving part of the side cartridge so that the upper cartridge assembly or lower cartridge assembly moves relative to the lower cartridge assembly or upper cartridge assembly to close the ligating clips in the upper cartridge assembly and lower cartridge assembly, and close the ligating clips until the upper and lower clamping mechanisms between the upper cartridge assembly and the lower cartridge assembly are stuck to the upper cartridge assembly and the lower cartridge assembly before the ligating clips are completely closed;

(5) Remove the side cartridge from a side of the upper cartridge assembly and the lower cartridge assembly to obtain a fully closed cartridge that can be placed into a continuous firing clip applier.

* * * * *